United States Patent
Oguni et al.

(10) Patent No.: US 7,892,850 B2
(45) Date of Patent: Feb. 22, 2011

(54) APPARATUS AND METHOD FOR MEASURING IMMATURE PLATELETS

(75) Inventors: Shinichiro Oguni, Akashi (JP); Seido Biwa, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 987 days.

(21) Appl. No.: 10/883,602

(22) Filed: Jul. 1, 2004

(65) Prior Publication Data
US 2005/0002826 A1 Jan. 6, 2005

(30) Foreign Application Priority Data
Jul. 4, 2003 (JP) .............................. 2003-192494

(51) Int. Cl.
G01N 21/76 (2006.01)
G01N 31/00 (2006.01)
G01N 33/48 (2006.01)
G01N 21/00 (2006.01)

(52) U.S. Cl. .............................. 436/172; 436/8; 436/63; 356/73

(58) Field of Classification Search ................... 436/63, 436/72, 10; 356/73
See application file for complete search history.

(56) References Cited

U.S. PATENT DOCUMENTS

| 5,369,661 A | * | 11/1994 | Yamaguchi et al. | ........... 372/69 |
| 5,821,127 A | * | 10/1998 | Akai et al. | .................... 436/10 |
| 6,133,995 A | | 10/2000 | Kubota | |
| 6,228,652 B1 | * | 5/2001 | Rodriguez et al. | ............ 436/63 |

FOREIGN PATENT DOCUMENTS

| JP | 11-006831 | | 1/1999 |
| JP | 11-258232 | * | 9/1999 |

* cited by examiner

Primary Examiner—Jill Warden
Assistant Examiner—Dean Kwak
(74) Attorney, Agent, or Firm—Brinks Hofer Gilson & Lione

(57) ABSTRACT

An apparatus for measuring immature platelets is described that includes (a) a sample preparation unit for preparing an assay sample by adding a reagent to a blood specimen; (b) a detection unit having a semiconductor laser light source for irradiating the assay sample with laser light, and a detector for detecting optical information emitted from particles within the assay sample irradiated by laser light; and (c) a controller for differentiating and counting immature platelets based on the detected optical information. A method for measuring immature platelets is also described.

9 Claims, 9 Drawing Sheets

APPARATUS AND METHOD FOR MEASURING IMMATURE PLATELETS

This application claims priority under 35 U.S.C. §119 to Japanese Patent Application No. 2003-192494, filed Jul. 4, 2003, the entire content of which is hereby incorporated by reference.

FIELD OF THE INVENTION

The present invention relates to an improved and compact device for measuring immature platelets, which automatically detects and counts immature platelets in a blood specimen. In the present invention, "immature platelet" refers to a platelet at the immature stage, which includes comparatively plentiful RNA within the cell during the process in which the platelet cell differentiates from a megakaryocyte precursor cell to a matured platelet. This concept includes reticulated platelets. Furthermore, in the present invention, normal platelets present in peripheral blood are referred to as "mature platelets" in relation to immature platelets.

BACKGROUND

The measurement of reticulated platelets, that is immature platelets, is considered to reflect the platelet production function in the marrow, and has been reported to be useful in differentiating idiopathic thrombocytopenic purpura (ITP) and other thrombopenic diseases (for example, aplastic anemia (AA)). Furthermore, the measurement of reticulated platelets has been reported to be useful as a platelet recovery index after chemotherapy and stem cell transplantation.

Conventional methods for measuring immature platelets typically produce an assay sample by reacting platelets in a blood specimen with an anti-platelet antibody treated with a fluorescent marker, and fluorescently staining the platelets with fluorescent dye, then measuring the platelets with a flow cytometer. This method takes a comparatively long time for the antigen-antibody reaction and fluorescent staining, and the work of producing the sample is complex.

An example of an automatic measuring apparatus providing a simpler method for measuring immature platelets is disclosed in U.S. Pat. No. 6,133,995. It describes a device in which olamin-O, a fluorescent dye that bonds with cellular RNA, is used to fluorescently stain platelets in the blood, the fluorescently stained blood sample flows through a flow cell, and the particles in the blood sample flowing through the flow cell are irradiated by an argon ion laser beam, then the scattered light and fluorescent light generated from each particle are detected and analyzed to differentiate and count the reticulated platelets.

An argon ion laser light source is used in the device disclosed in U.S. Pat. No. 6,133,995. However, the argon ion laser light source is extremely expensive. Furthermore, the entire device is made larger in scale because the argon ion laser light source is large. However, the olamin-O and other usable materials disclosed in the same publication, that is, acridine orange, propidium iodide, ethidium bromide, Hoechst 33342, pyronin Y, and rhodamine 123 used in the device disclosed in the embodiments in U.S. Pat. No. 6,133,995 are invariably fluorescent dyes which emit fluorescent light when excited by the wavelength of an argon ion laser. Therefore, when semiconductor laser light sources having a different excitation wavelength is used, it is difficult to measure the reticulated platelets using the various fluorescent dyes.

SUMMARY

The scope of the present invention is defined solely by the appended claims, and is not affected to any degree by the statements within this summary.

An apparatus for measuring immature platelets embodying features of the present invention includes (a) a sample preparation unit for preparing an assay sample by adding a reagent to a blood specimen; (b) a detection unit having a semiconductor laser light source for irradiating the assay sample with laser light, and a detector for detecting optical information emitted from particles within the assay sample irradiated by laser light; and (c) a controller for differentiating and counting immature platelets based on the detected optical information.

A method for measuring immature platelets embodying features of the present invention includes (a) preparing an assay sample by adding a reagent to a blood specimen; (b) irradiating the assay sample with laser light by using a semiconductor laser light source; (c) detecting optical information emitted from particles within the assay sample irradiated by laser light; and (d) differentiating and counting immature platelets based on the detected optical information.

DETAILED DESCRIPTION OF THE DRAWINGS AND THE PRESENTLY PREFERRED EMBODIMENTS

As a result of diligent investigation, the present inventors succeeded in finding a fluorescent dye which produces different staining characteristics between immature platelets and mature platelets, and which is excitable by a laser beam emitted from a semiconductor light source. In this way, the present inventors have invented an apparatus for measuring immature platelets, which prepares an assay sample using a staining reagent containing the aforesaid fluorescent dye, irradiates the prepared assay sample with laser light using a semiconductor light source, and detects optical information emitted from the assay sample, then classifies and counts the immature platelets (this concept includes reticulated platelets).

The following examples and representative procedures illustrate features in accordance with the present invention, and are provided solely by way of illustration. They are not intended to limit the scope of the appended claims or their equivalents.

The embodiments of the apparatus for measuring immature platelets of the present invention are described below. This apparatus uses whole blood as the specimen. An assay sample which has been subjected to dilution and staining processes is prepared from the specimen, and optical information of fluorescent light and forward scattered light are detected from each particle, that is the immature platelets and mature platelets, in the assay sample using a flow cytometer. Then, the immature platelets and mature platelets included in the specimen are counted by analyzing the aforesaid optical information.

Figure 1:
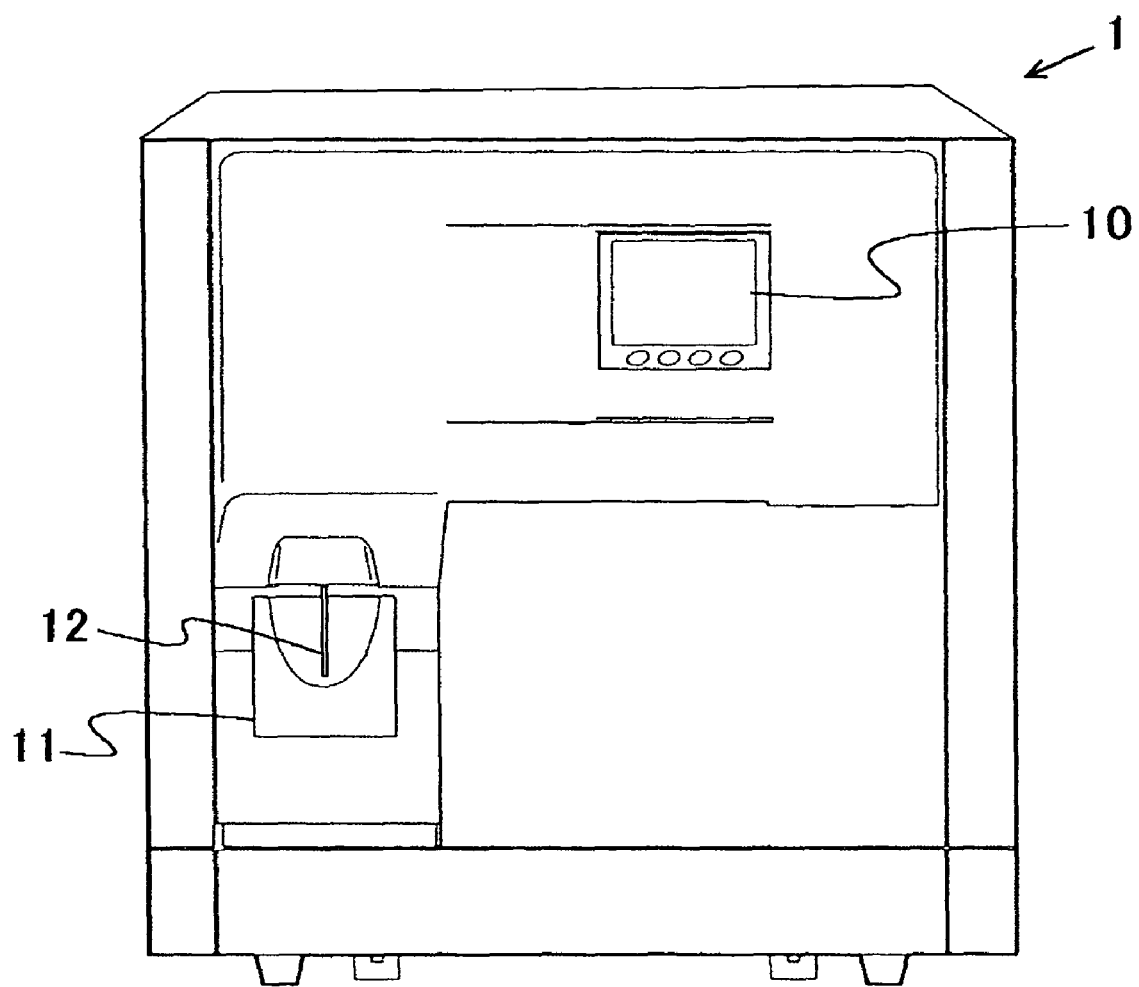
FIG. 1 shows an external view of an apparatus for measuring immature platelets embodying features of the present invention.

FIG. 1 shows an external view of the apparatus for measuring immature platelets. The front surface of the apparatus for measuring immature platelets 1 is provided with a liquid crystal touch panel 10 for displaying assay results and used by an operator to input various types of settings, a start switch 11 for starting an assay operation, and a probe 12 for suctioning a specimen.

Figure 2:
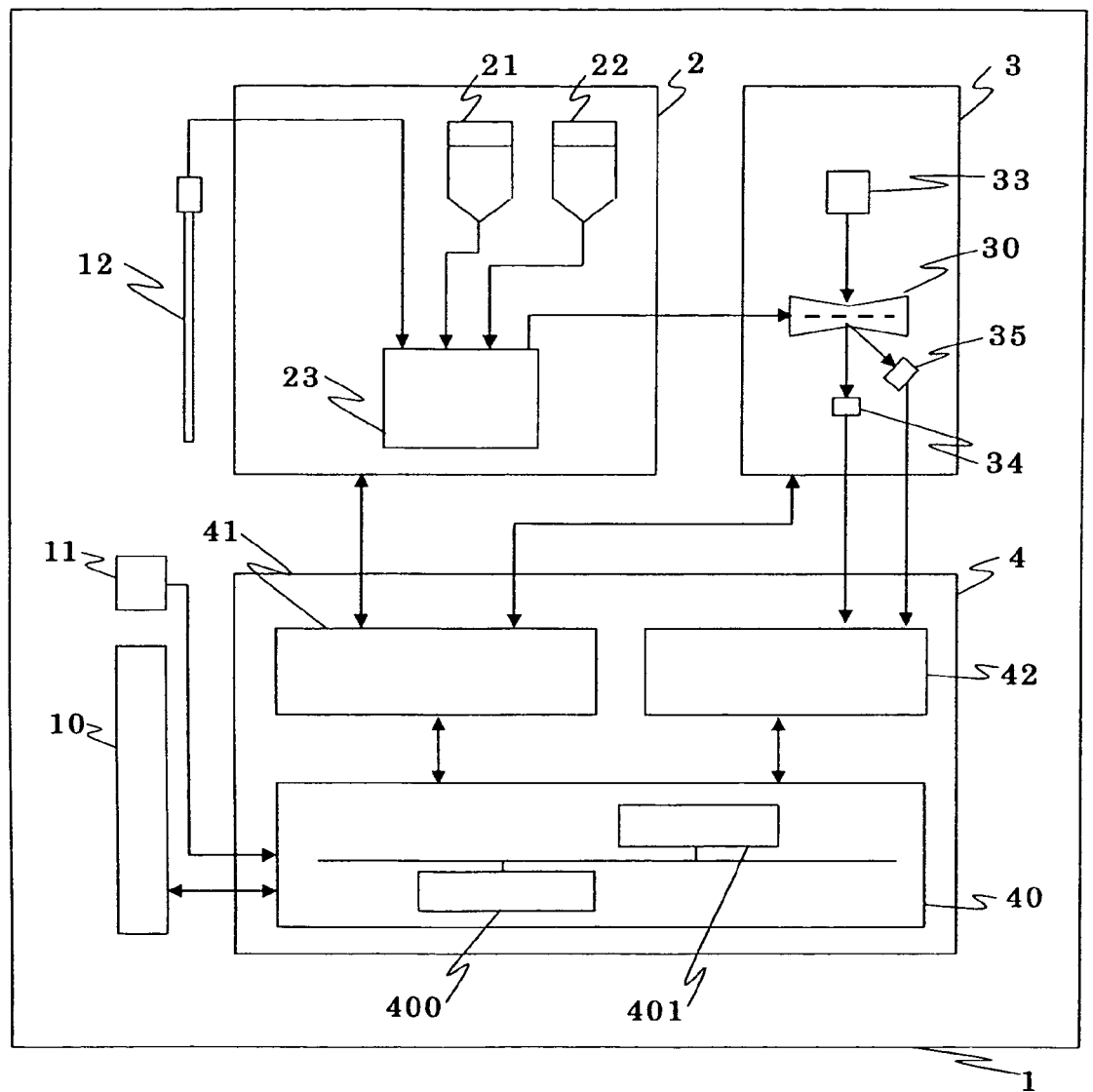
FIG. 2 shows the functional structures of the apparatus for measuring immature platelets embodying features of the present invention.

FIG. 2 is a diagram of the functional structures of the apparatus for measuring immature platelets 1. The apparatus for measuring immature platelets 1 is provided with a sample preparation unit 2, detection unit 3, and control unit 4.

The sample preparation unit 2 is provided with a dilution fluid container 21 for accommodating a dilution fluid used for diluting a specimen, staining fluid container 22 for accommodating a staining fluid used for staining a specimen, and a reaction vessel 23 for mixing the dilution fluid, staining fluid, and a specimen suctioned through the probe 12. The reaction vessel 23 has a mixing mechanism and a temperature control mechanism not shown in the drawing. In this way the fluids within the vessel are mixed for a predetermined time while maintaining a constant temperature, so as to prepare an assay sample. The probe 12, dilution fluid container 21, and staining fluid container 22 are connected with the reaction vessel 23 through tubes. Furthermore, the reaction vessel 23 is connected to a flow cell of the detection unit 3, which is described later, through a tube. A pump and valve not shown in the drawing are provided for each tube. The specimen, dilution fluid, and staining fluid are respectively supplied to the reaction vessel 23, and the prepared assay sample within the reaction vessel 23 is supplied to the detection unit 3 by controlling these pumps and valves.

The detection unit 3 is provided with a flow cell 30 through which flows the assay sample, semiconductor laser light source 33 for irradiating an assay sample within the flow cell with laser light, photodiode 34 for detecting the forward scattered light emitted from the particles in the assay sample irradiated by the laser light, and a photomultiplier tube 35 for detecting the fluorescent light emitted from the particles in the assay sample irradiated by laser light.

Figure 3:
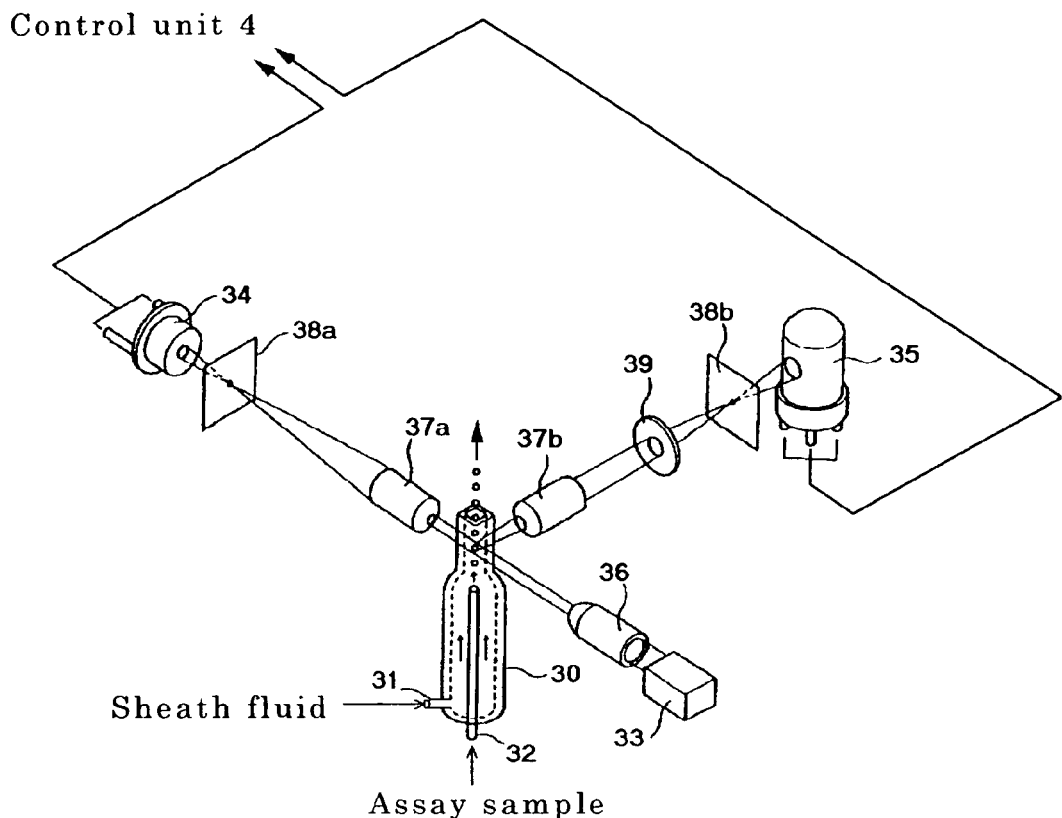
FIG. 3 illustrates the measuring unit of the apparatus for measuring immature platelets embodying features of the present invention.

FIG. 3 shows a perspective view of the detection unit 3. The flow cell 30 is a tube through which flows an assay sample prepared by the sample preparation unit 2 and a sheath fluid supplied from a sheath fluid container not shown in the drawing. The sheath fluid flows so as to surround the flow of the assay sample when the assay sample flows through the flow cell 30. The sheath fluid is introduced into the flow cell 30 through a sheath fluid inlet 31. The assay sample is discharged from a sample nozzle 32 into the center of the sheath fluid flow within the flow cell 30. In this way the assay sample is surrounded by the sheath fluid within the flow cell 30, so as to flow in a narrowly restricted state.

Furthermore, the detection unit 3 is provided with a light source 33 for irradiating an assay sample flowing through the flow cell 30 with laser light, and a photodiode 34 and photomultiplier tube 35 for respectively receiving the forward scattered light and fluorescent light emitted from the particles within the assay sample irradiated by the laser light. The light source 33 is a red color semiconductor laser light source, which emits a laser beam at a wavelength of 633 nm. The semiconductor light source is advantageous inasmuch as it is compact compared to an argon ion laser light source, and has a long generating service life. A condenser lens 36 is arranged on the optical axis between the light source 33 and the flow cell 30, and a converging lens 37a and pinhole 38a are arranged on the optical axis between the flow cell 30 and the photodiode 34. A converging lens 37b, optical filter 39, and pinhole 38b are arranged on the optical axis between the flow cell 30 and the photomultiplier tube 35. The photodiode 34 outputs electrical signals (forward scattered light signals) corresponding to the intensity of the received forward scattered light. Furthermore, the photomultiplier tube 35 outputs electrical signals (fluorescent light signals) corresponding to the intensity of the received fluorescent light. The forward scattered light signals and fluorescent light signals obtained by the detection unit 3 are transmitted to the control unit 4.

The control unit 4 is provided with a microcomputer 40 which includes a central processing unit 400 and a memory 401, a control circuit 41 for controlling the operation of each unit of the apparatus for measuring immature platelets 1, and a signal processing circuit 42 for subjecting the forward scattered light signals and fluorescent light signals sent from the detection unit 3 to a noise elimination process and extracting the required data. Stored in the memory 401 are control programs for controlling the operation of each part of the apparatus for measuring immature platelets 1 through the control circuit 41 and executing the series of assay operations, and analysis programs for analyzing the extracted data processed by the signal processing circuit 42 and counting the immature platelets and mature platelets contained in the specimen. The analysis results obtained by the analysis program are output to the liquid crystal touch panel 10 provided on the front of the apparatus for measuring immature platelets 1.

Figure 4:
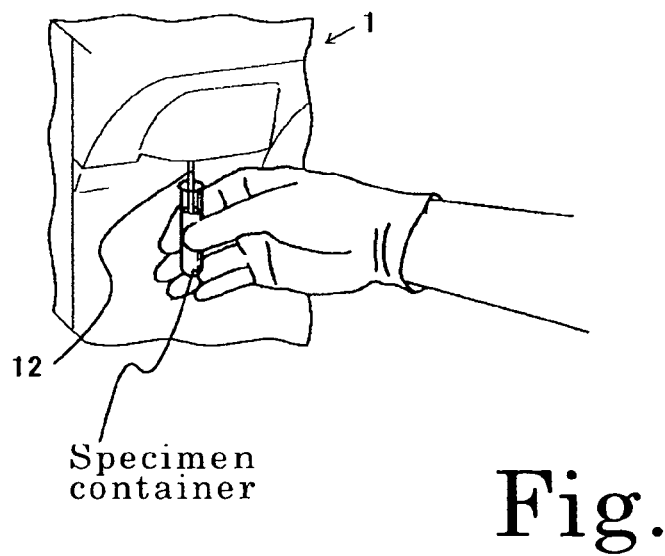
FIG. 4 illustrates the situation of suctioning a specimen from the probe in the apparatus for measuring immature platelets embodying features of the present invention.
Figure 5:
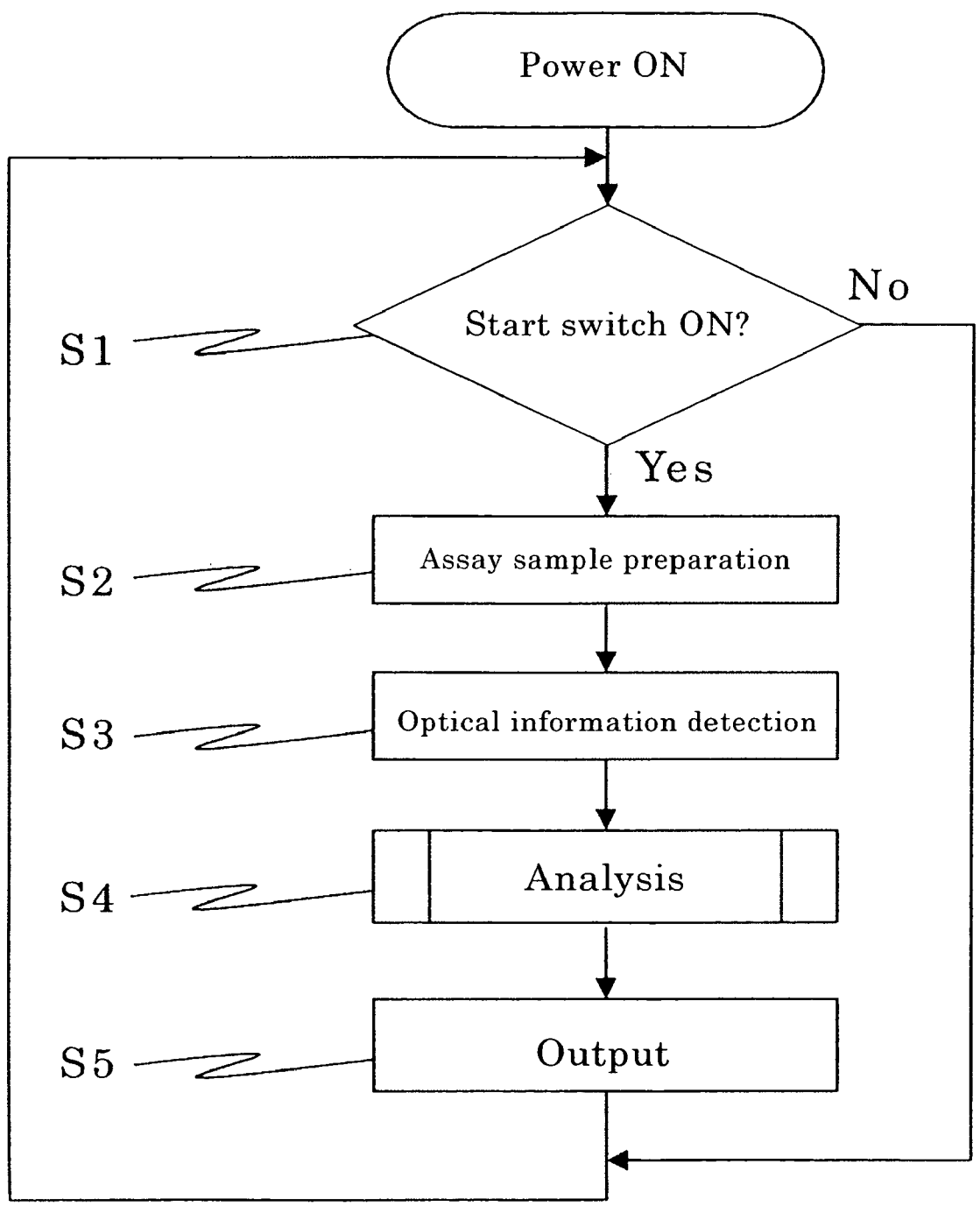
FIG. 5 is a flow chart of the automatic operation controls of the apparatus for measuring immature platelets embodying features of the present invention.

The operation of the apparatus for measuring immature platelets 1 is described below. FIG. 5 is a flow chart showing the essential operation of the apparatus for measuring immature platelets 1. First, the power supply of the apparatus for measuring immature platelets 1 is turned ON by an operator. This operation starts the control program stored in the memory 401 of the control unit 4, which thereafter controls the operation of the apparatus for measuring immature platelets 1. Then, as shown in FIG. 4, when the tip of the probe 12 has been inserted below the surface of the specimen fluid accommodated in the specimen container, the operator presses the start switch 11 (S1). In this way each step, including the assay sample preparation (S2), optical information detection (S3), analysis (S4), and output (S5), is automatically and sequentially executed in the apparatus for measuring immature platelets 1. The operations performed in each unit of the apparatus for measuring immature platelets 1 in steps S2, S3, S4, and S5 are described below.

Assay Sample Preparation (S2)

In S2, the sample preparation unit 2 is controlled to prepare an assay sample from the specimen and predetermined reagents. As shown in FIG. 4, when the tip of the probe 12 has been inserted below the surface of the specimen fluid accommodated in the specimen container, the apparatus for measuring immature platelets 1 suctions the specimen in the specimen container from the tip of the probe 12. From the suctioned specimen, 4.5 µL of the specimen is discharged into the reaction vessel 23 of the sample preparation unit 2 through a tube. Then, 0.8955 mL of dilution fluid is supplied from the dilution fluid container 21 to the reaction vessel 23 through a tube, and the specimen is diluted. Next, 18 µL of staining fluid is supplied from the staining fluid container 22 to the reaction vessel 23 through a tube. Thereafter, the fluid temperature is maintained at 40° C. while the fluids are mixed for 31 seconds to stain the diluted specimen. The staining fluid used includes a polymethene fluorescent dye represented by the structural formula below.

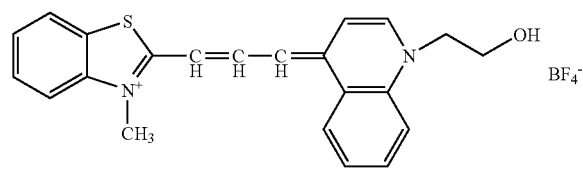

This fluorescent dye possesses the property of producing fluorescence when excited by a laser light having a wavelength of approximately 633 nm. That is, fluorescence is excited by the red color laser light emitted from the light source 33 of the detection unit 3. This fluorescent dye has a further property of bonding with RNA in cells. Therefore, a difference in stainability occurs between cells having a large RNA content (for example, immature platelets) and cells having a low RNA content (for example, mature platelets), such that there is also a difference in the intensities of the fluorescence detected in S3, which is described later.

Optical Information Detection (S3)

In S3, flow cytometery is used to detect the forward scattered light and fluorescent light as optical information from each particle in the assay sample fluid.

First, the sheath fluid accommodated within a sheath fluid container not shown in the drawing is introduced into the flow cell 30 through a tube, so as to flow. Then, a prepared assay sample is sent to the flow cell 30 from the reaction vessel 23 of the sample preparation unit 2, and discharged into the flow cell 30 through the sample nozzle 32. In this way the assay sample is surrounded in the sheath fluid within the flow cell 30, and flows in a narrowly restricted state.

Then, the light source 33 is actuated, and the emitted laser light irradiates the assay sample flowing through the flow cell 30. The laser light emitted from the laser light source 33 is converged on the flow cell 30 by the condenser lens 36. The forward scattered light emitted from the particles in the assay sample irradiated by the laser light is focused by the converging lens 37a, and enters the photodiode 34 through the pinhole 38a. The fluorescent light emitted from the particles in the assay sample irradiated by the laser light is focused by the converging lens 37b, and enters the photomultiplier tube 35 through the optical filter 39 and pinhole 38b. The photodiode 34 and photomultiplier tube 35 respectively output forward scattered light signals and fluorescent light signals. These electrical signals are transmitted to the control unit 4. The intensity of the forward scatter light signal (intensity of the forward scattered light) is information which reflects the size of the cells, such that the larger the cell, the greater is the obtained forward scattered light intensity. The intensity of the fluorescent light (fluorescent light intensity) is information which reflects the degree of fluorescent staining of the cell. That is, in the apparatus for measuring immature platelets 1 of the present embodiment of the present invention which uses a staining reagent that contains a fluorescent dye having the property of bonding with the RNA within the cells, the greater the RNA content of the cell, the higher is the fluorescent intensity.

S4 (Analysis)

In S4, the forward scattered light signals and fluorescent light signals input from the detection unit 3 are processed and analyzed in the control unit 4. First, the forward scattered light signals and fluorescent light signals are input to the signal processing circuit 42. The signal processing circuit 42 removes noise signals from the forward scattered light signals and fluorescent light signals, and obtains forward scattered light data and fluorescent light data corresponding to each particle. The data are input to the microcomputer 40.

Figure 6:
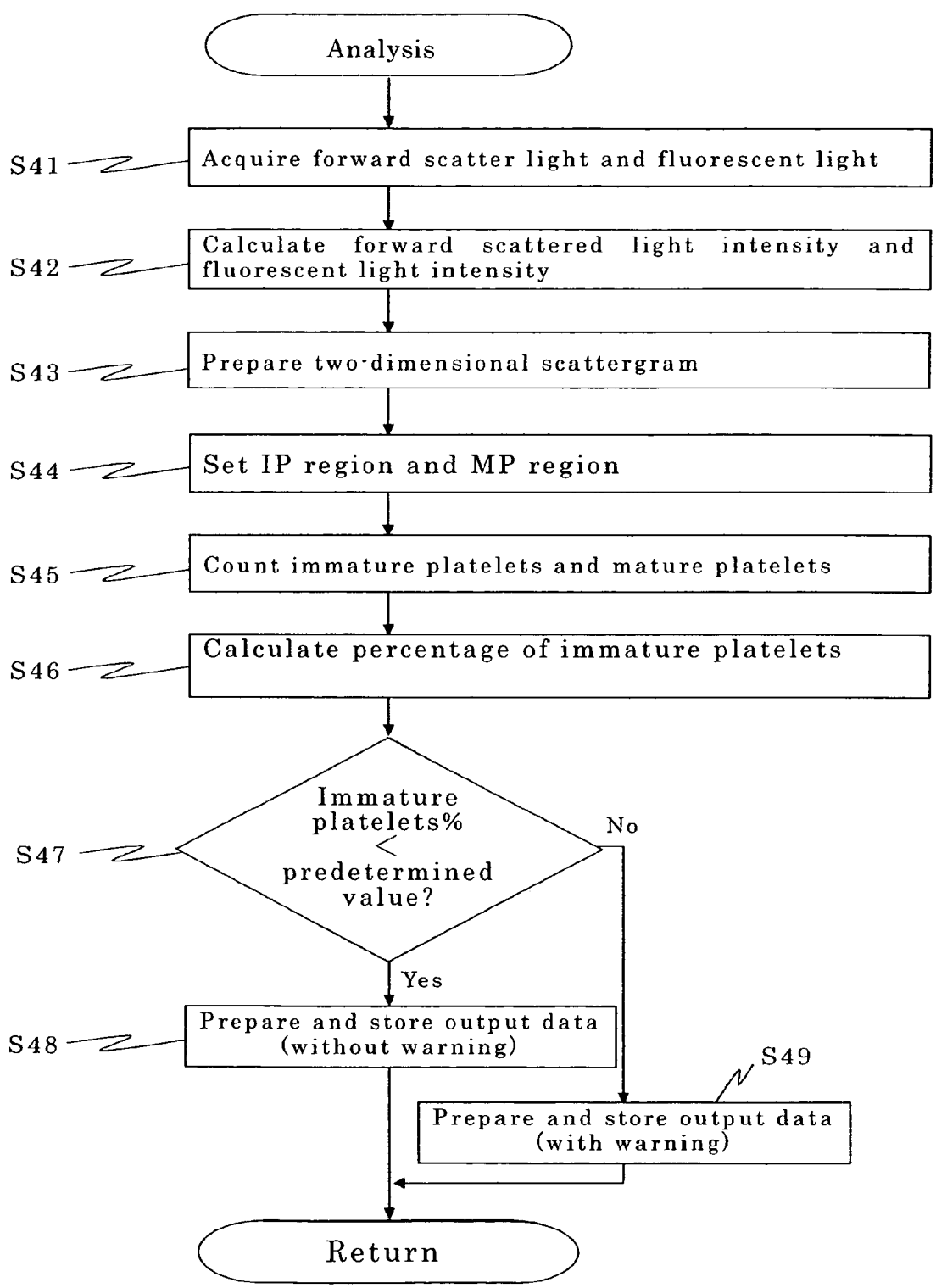
FIG. 6 is a flow chart of the analysis performed by the apparatus for measuring immature platelets embodying features of the present invention.

The microcomputer 40 starts the analysis program stored in the memory 401, and analyzes the data input from the signal processing circuit 42. The flow of the analysis program is described below based on FIG. 6.

S41: Forward scattered light data and fluorescent light data corresponding to each particle in the assay sample are acquired from the signal control circuit 42.

S42: The forward scattered light intensity and fluorescent light intensity of each particle in the assay sample is calculated based on the data acquired in S41.

S43: Two-dimensional coordinates are developed using the forward scattered light intensity and fluorescent light intensity as axes. Then, dots are placed on the coordinate positions corresponding to the forward scattered light intensity and fluorescent light intensity of each particle in the assay sample calculated in S42. In this way a two-dimensional scattergram is prepared using the forward scattered light intensity and fluorescent light intensity as parameters.

S44: The region IP in which the immature platelets appear and the region MP in which the mature platelets appear are set on the two-dimensional scattergram prepared in S43. The region IP and region MP have been experimentally determined by measuring the forward scattered light intensity and fluorescent light intensity from assay samples containing cells confirmed beforehand to be mature platelets and cells confirmed beforehand to be immature platelets by microscopic examination and the like. In this way the coordinate data of the IP region and MP region determined beforehand are stored in the memory 401, and read by the analysis program in S44 so as to be applied to the two-dimensional scattergram.

S45: The number of dots which appear in the region IP and the region MP, respectively, set in S44 is counted. The number of dots appearing in the region IP represents the number of immature platelets in the sample, and the number of dots appearing in the region MP represents the number of mature platelets in the specimen.

S46: The total number of immature platelets and mature platelets determined in S45 (total platelets) is determined. Then, the number of immature platelets is divided by the determined total number of platelets. In this way the percentage of immature platelets is determined (percentage of immature platelets=number of immature platelets/(number of immature platelets+number of mature platelets)).

S47: the percentage of immature platelets determined in S46 is compared to a predetermined value. When the percentage of immature platelets is lower than the predetermined value, the routine continues to S48. When the percentage of immature platelets is higher than the predetermined value, the routine continues to S49.

The predetermined value compared to the percentage of immature platelets in S47 is stored beforehand in the memory 401. This predetermined value is read by the analysis program in S47, and compared to the percentage of immature platelets determined in the assay of the specimen. When the percentage of immature platelets exceeds the predetermined value, the possibility of a specific disease (in this case, idiopathic thrombocytopenic purpura (ITP)) is suggested by outputting a warning to the operator of the apparatus for measuring immature platelets 1 in a manner described later.

S48: The previously prepared two-dimensional scattergram, determined number of immature platelets, number of mature platelets, and percentage of immature platelets are stored in the memory 401 and prepared as output data for outputting to the liquid crystal touch panel 10 in S5 (output) described later.

S49: A warning summarizing the previously prepared two-dimensional scattergram, determined number of immature platelets, number of mature platelets, percentage of immature platelets, and that the percentage of immature platelets exceeds the predetermined value is stored in the memory 401 and output data are prepared for outputting to the liquid crystal touch panel 10 in step S5 (output) described later.

Figure 7:
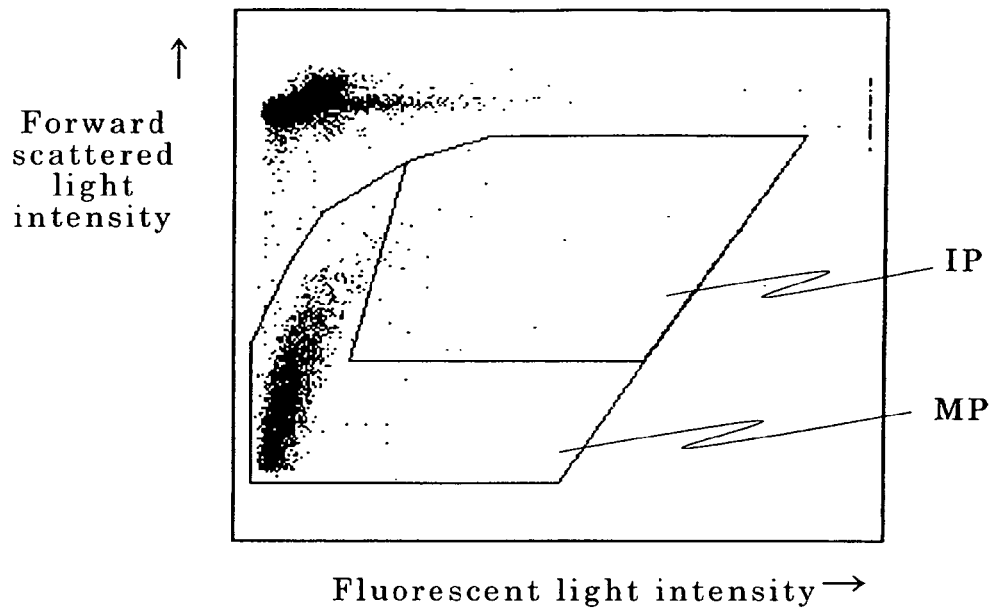
FIG. 7 shows an example of a two-dimensional scattergram output by the apparatus for measuring immature platelets embodying features of the present invention.

An example of the two-dimensional scattergram prepared in S43 and S44 is shown in FIG. 7. This two-dimensional scattergram plots the forward scattered light intensity on the vertical axis, and the fluorescent light intensity on the horizontal axis. The region IP in which the immature platelets appear, and the region MP in which the mature platelets appear, are set. The immature platelets have a greater RNA content within the cell than do mature platelets, and they are larger than the mature platelets. Therefore, the region IP is set at a higher position of forward scattered light and fluorescent light intensities compared to the region MP.

S5 (Output)

Figure 13:
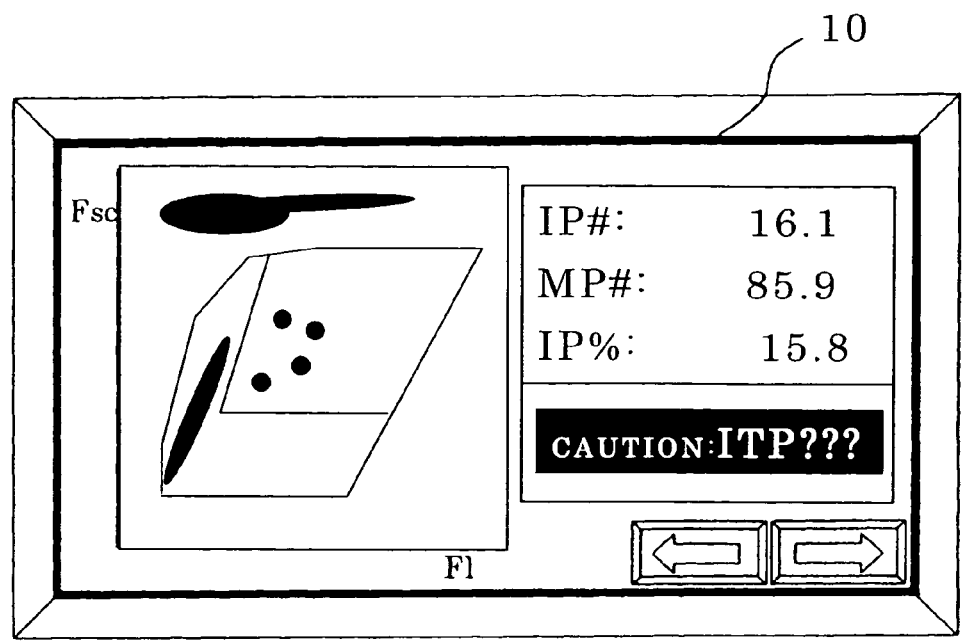
FIG. 13 shows the situation of data output to a liquid crystal touch panel of the apparatus for measuring immature platelets embodying features of the present invention.

The control unit 4 outputs the data prepared in S48 and S49 and stored in the memory 401 in S4 (analysis) to the liquid crystal touch panel 10. FIG. 13 shows the situation when the data stored in the memory 401 is output to the liquid crystal touch panel 10. The prepared two-dimensional scattergram, determined number of immature platelets, number of mature platelets, and percentage of immature platelets are displayed on the liquid crystal touch panel 10. When the comparison of the percentage of immature platelets and the predetermined value results in the percentage of immature platelets being a value higher than the predetermined value, a warning indicating that there is a high possibility that the assayed specimen is from a patient with idiopathic thrombocytopenic purpura is displayed together with the prepared two-dimensional scattergram, determined number of immature platelets, number of mature platelets, and percentage of immature platelets. FIG. 13 also shows the situation when a warning is output.

ASSAY RESULT EXAMPLE 1

Figure 8:
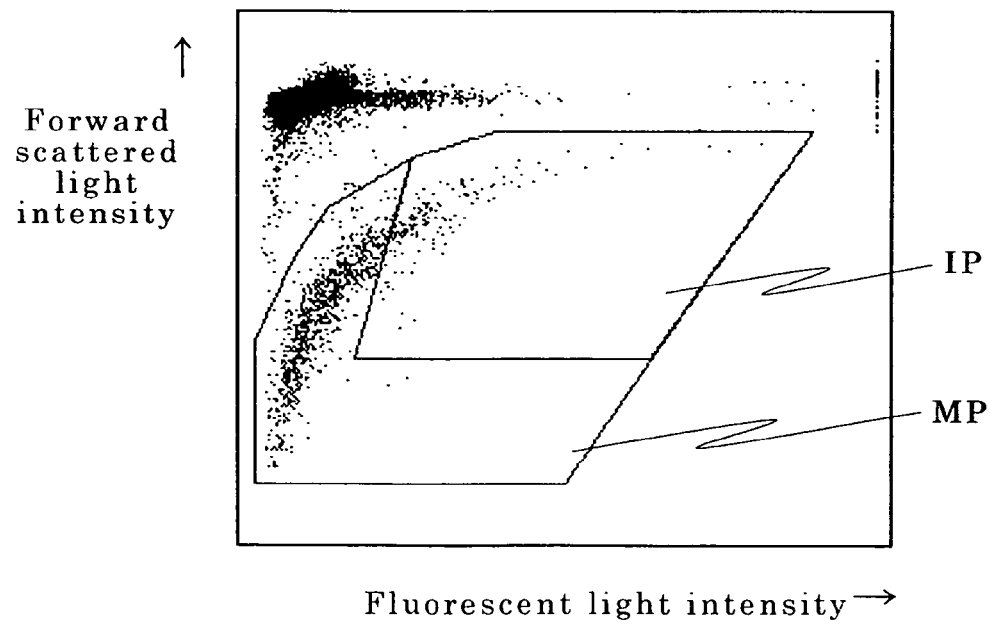
FIG. 8 shows an example of a two-dimensional scattergram output by the apparatus for measuring immature platelets embodying features of the present invention.
Figure 9:
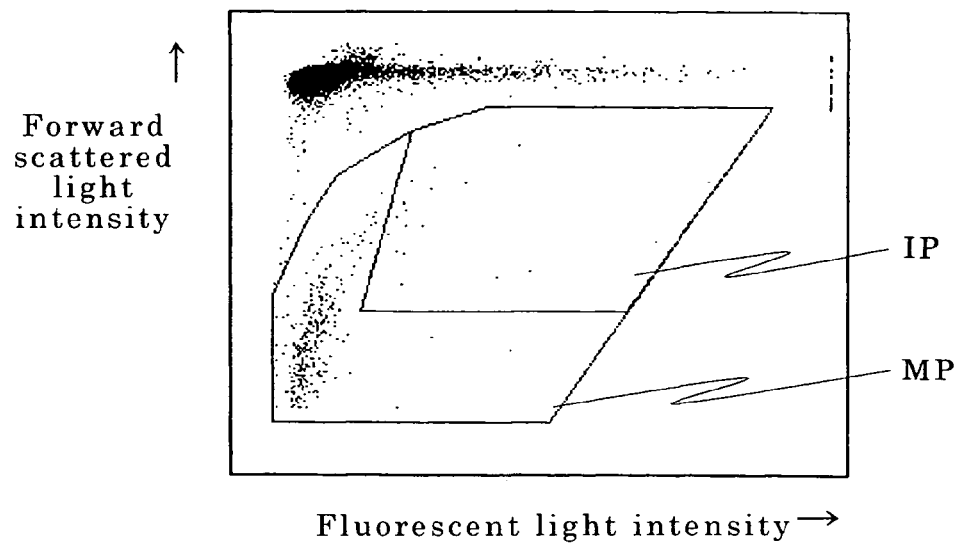
FIG. 9 shows an example of a two-dimensional scattergram output by the apparatus for measuring immature platelets embodying features of the present invention.

FIG. 7 is a two-dimensional scattergram resulting from assaying blood collected from a healthy subject using the apparatus for measuring immature platelets 1 described above. Furthermore, FIG. 8 is a two-dimensional scattergram resulting from assaying blood collected from a patient with idiopathic thrombocytopenic purpura (ITP) using the apparatus for measuring immature platelets 1. FIG. 9 is a two-dimensional scattergram resulting from assaying blood collected from a patient with aplastic anemia (AA) using the apparatus for measuring immature platelets 1. Both ITP and AA are diseases having a reduced platelet count. Each of the two-dimensional scattergrams is analyzed in the apparatus for measuring immature platelets 1, and the acquired number of immature platelets, number of mature platelets, and percentage of immature platelets are shown in Table 1.

TABLE 1

|  | No. immature platelets ($\times 10^9$/L) | No. mature platelets ($\times 10^9$/L) | Percentage immature platelets (%) |
| --- | --- | --- | --- |
| Healthy subject (FIG. 7) | 4.9 | 210.1 | 2.3 |
| ITP patient (FIG. 8) | 16.1 | 85.9 | 15.8 |
| AA patient (FIG. 9) | 1.9 | 28.1 | 6.3 |

From Table 1 and FIGS. 7 and 8 it can be understood that ITP patients have more immature platelets in the blood than do healthy subjects. This condition is thought to be a result of elevated production of immature platelets in ITP patients, which causes platelets in an immature state to appear in peripheral blood. Although a slight elevation in the percentage of immature platelets is observed AA patients compared to healthy subjects in Table 1, a comparison of FIGS. 8 and 9 reveal that the strong presence of immature platelets emitting a fluorescent light observed in ITP patients is not seen in AA patients. In this way the two-dimensional scattergram, number of immature platelets, number of mature platelets, and percentage of immature platelets prepared by the apparatus for measuring immature platelets 1 provide useful information which allows discrimination between ITP and AA, which are diseases with reduced platelet levels.

ASSAY RESULT EXAMPLE 2

Figure 10:
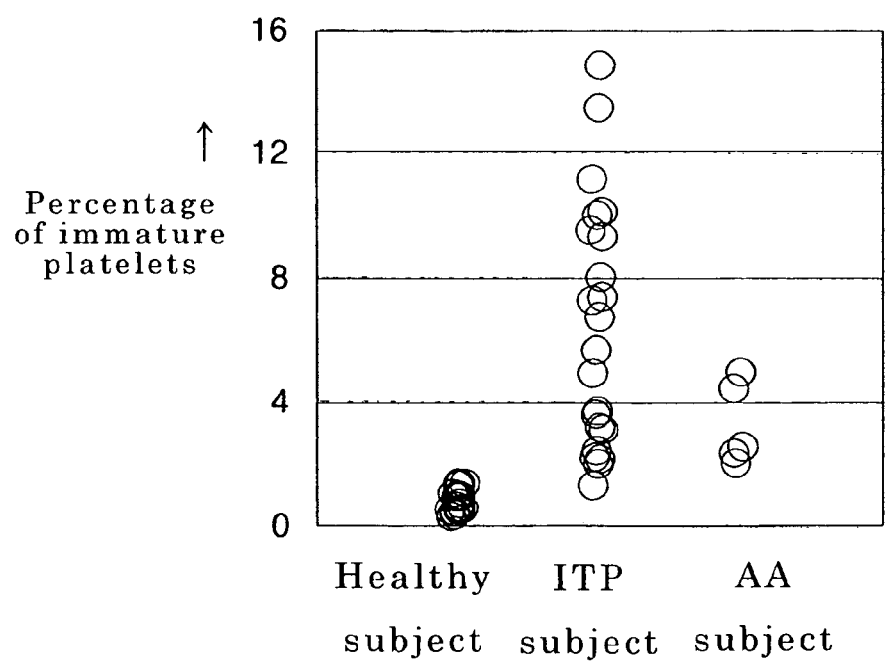
FIG. 10 is a graph showing the percentages of immature platelets obtained by measuring the blood collected from a plurality of healthy donors, ITP donors, and AA donors using the apparatus for measuring immature platelets embodying features of the present invention.

FIG. 10 is a graph showing the percentage of immature platelets in blood specimens collected from 18 healthy subjects, 22 ITP patients, and 6 AA patients using the apparatus for measuring immature platelets 1, as differentiated by each type of subject and disease. ITP patients showed significantly higher values for the percentage of immature platelets. From this information it is understood that the percentage of immature platelets obtained by the apparatus for measuring immature platelets 1 is useful in discriminating ITP.

ASSAY RESULT EXAMPLE 3

Figure 11:
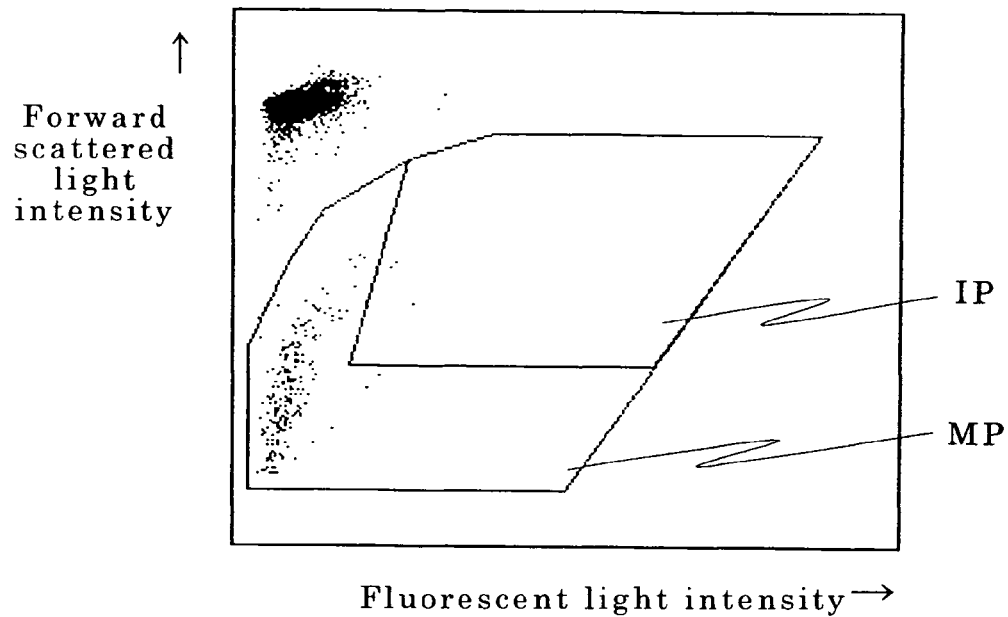
FIG. 11 shows an example of a two-dimensional scattergram output by the apparatus for measuring immature platelets embodying features of the present invention.
Figure 12:
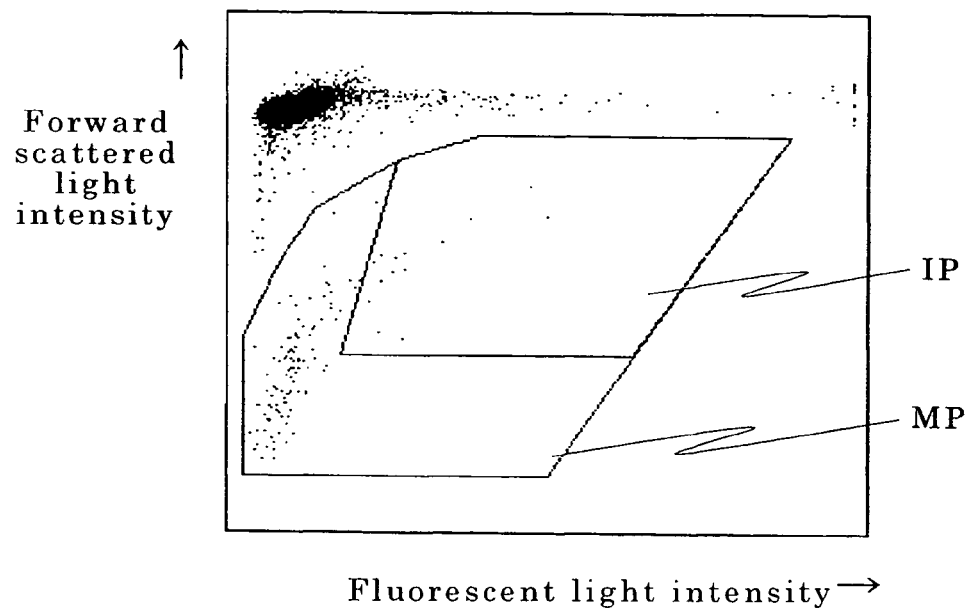
FIG. 12 shows an example of a two-dimensional scattergram output by the apparatus for measuring immature platelets embodying features of the present invention.

FIGS. 11 and 12 are two-dimensional scattergrams prepared by the apparatus for measuring immature platelets 1 from blood collected from a patient with hematopoietic tumor. FIG. 11 shows the result of assay of blood collected from the aforesaid patient in the nadir stage of chemotherapy. FIG. 12 shows the result of the assay of blood collected from the aforesaid patient after bone marrow transplantation following continuous chemotherapy when the number of immature platelets has increased to a maximum after transplantation. Each two-dimensional scattergram was analyzed in the apparatus for measuring immature platelets 1, and the calculated number of immature platelets, number of mature platelets, and percentage of immature platelets are shown in Table 2.

TABLE 2

|  | No. immature platelets (×10⁹/L) | No. mature platelets (×10⁹/L) | Percentage immature platelets (%) |
| --- | --- | --- | --- |
| Nadir stage (FIG. 11) | 0.3 | 22.7 | 1.3 |
| Max No. immature platelets stage FIG. 12) | 1.4 | 10.6 | 11.7 |

It is clear from FIGS. 11 and 12 that immature platelets were conspicuously absent in the specimen from the patient in the nadir stage of continuous chemotherapy. This condition is thought to reflect the reduced platelet production function in patients in the nadir stage of chemotherapy which results in inhibited marrow function and reduced platelet production.

The fluorescent dye used in the present invention is not limited to the fluorescent dye used in the previously described embodiment, and may be another fluorescent dye insofar as the dye is excitable by laser light from a semiconductor light source and produces a difference in stainability between immature platelets and mature platelets, that is, the fluorescent dye is capable of binding with the RNA contained within a cell so as to stain the cell. Furthermore, the fluorescent dye used with the red color semiconductor laser in the previously described embodiment is not limited to the fluorescent dye represented in the aforesaid embodiment, and may be, for example, a fluorescent dye represented by the structural formula below.

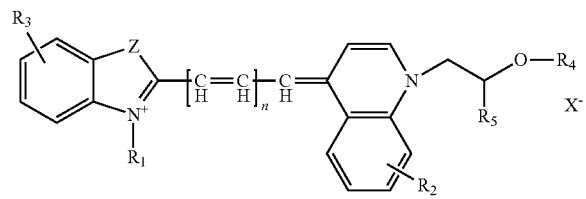

In the formula, R1 represents a hydrogen atom or lower alkyl group; R2 and R3 respectively represent a hydrogen atom, lower alkyl group or lower alkoxy group; R4 represents a hydrogen atom, acyl group, or lower alkyl group, R5 represents a hydrogen atom or substituted lower alkyl group; Z represents a sulfur atom, oxygen atom, or one or two lower alkyl group-substituted carbon atom; n represents 1 or 2; and X represents an anion. The lower alkyl group in R1 in the formula means an alkyl group having branched chain or straight chain of 1-6 carbon atoms, for example, methyl, ethyl, propyl, butyl, isobutyl, sec-butyl, tert-butyl, pentyl, and hexyl, among which methyl and ethyl are most desirable.

The lower alkyl groups in R2 and R3 are identical, and a lower alkoxy group means an alkoxy group having 1-6 carbon atoms, for example, methoxy, ethoxy, propoxy and the like, among which methoxy and ethoxy are desirable. R2 and R3 are most desirably hydrogen atoms. The acyl group in R4 is desirably an acyl group derived from aliphatic carboxylic acid, for example, acetyl, propionyl and the like, and among which an acetyl group is most desirable. Furthermore, the lower alkyl group is identical to that described above.

The lower alkyl group in R5 is identical to that described above, and in the case of a substituted lower alkyl group, a lower alkyl group with a substituted hydrogen atom, such as 1-3 hydroxyl groups, halogen atoms (for example, fluorine atom, chlorine atom, bromine atom, iodine atom) and the like, among which a methyl group or ethyl group substituted by one hydroxyl group is desirable. The lower alkyl group in Z is identical to that described above, and a sulfur atom is desirable as Z.

The anion in X may be a halogen ion (fluorine, chlorine, bromine, or iodine ion), halogenated boron (BF4-, BCl4-, BBr4- and the like), phosphided compound ion, halogen oxy-acid ion, fluorosulfonic acid ion, methylsulfonic acid ion, tetraphenylboron compound ions having halogen or an alkyl radical with halogen as a substitute radical in an aromatic ring and the like. Among these, bromine ion or BF4- is most desirable.

Although the apparatus for measuring immature platelets 1 classifies and counts the immature platelets and mature platelets in a specimen (whole blood) in the previously described embodiment, other types of particles contained in a specimen also may be classified and counted. For example red blood cells and reticulocytes may be classified and counted as the aforesaid particles.

Figure 14:
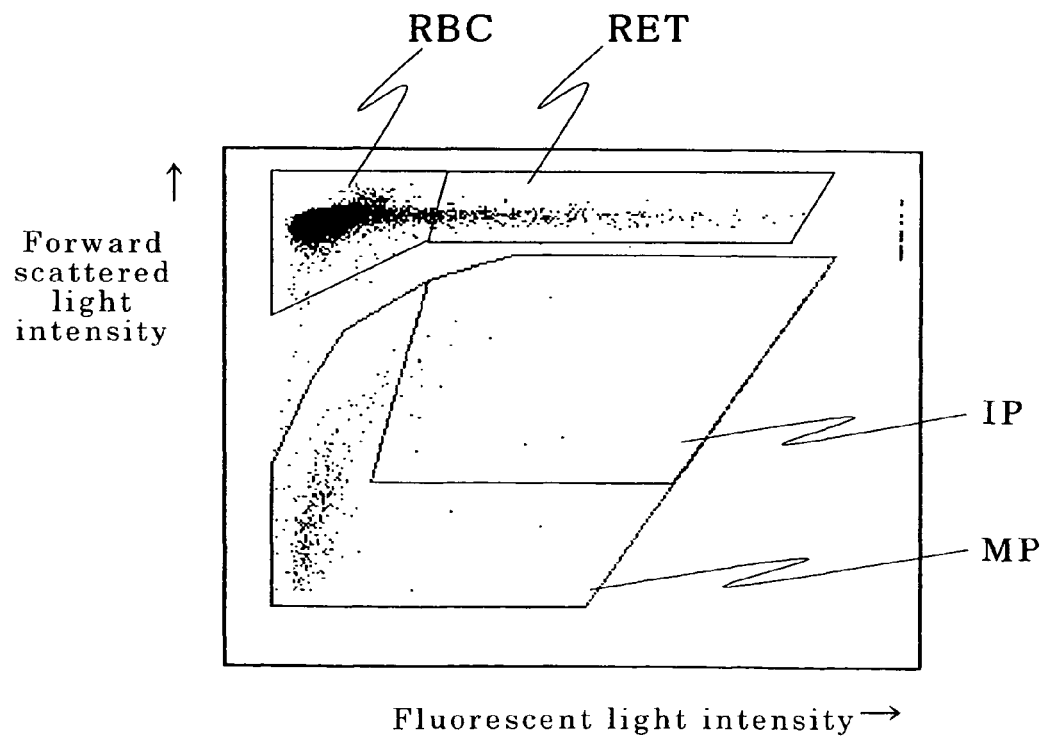
FIG. 14 shows an example of a two-dimensional scattergram output by the apparatus for measuring immature platelets embodying features of the present invention.

FIG. 14 is a two-dimensional scattergram obtained by assaying a blood specimen using the apparatus for measuring immature platelets 1; in this case, in addition to the region IP in which reticulated platelets appear, and the region MP in which mature platelets appear, a region RBC in which red blood cells appear and a region RET in which reticulocytes appear are also shown. In this case, the coordinate data of the region RBC and region RET are stored in the memory 401 of the apparatus for measuring immature platelets 1, and the analysis program in S44 reads the coordinate data of the region RBC and the region RET together with the coordinate data of the region IP and region MP so as to apply all the data to the two-dimensional scattergram. The reagents of the staining fluid and dilution fluid used in the present embodiment are identical to those of the previously described embodiment.

In the scattergram of FIG. 14, the region RBC and region RET are set at positions having greater forward scattered light intensity than the region IP and region MP. This condition is set because the red blood cells and reticulocytes are larger than the immature platelets and mature platelets. The region RET is set at a position of greater fluorescent light intensity than the region RBC. This condition is set because the reticulocytes, which are immature red blood cells, have RNA within the cells, and are more readily fluorescently stained than the mature red blood cells, which do not have RNA within the cells. In the present embodiment, not only are the reticulated platelets and mature platelets classified and counted, the red blood cells and reticulocytes are also classified and counted.

The present invention described above discriminates and counts immature platelets and mature platelets using a fluorescent dye which is excited by a semiconductor laser and which produces different staining properties between immature platelets and mature platelets. Therefore, the present invention provides an apparatus for measuring immature platelets capable of using a semiconductor laser as a light source which is less expensive and more compact than a conventional argon ion laser light source. In this way the apparatus for measuring immature platelets is easily rendered more compact.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. An apparatus for measuring immature platelets comprising:
    a sample preparation unit configured to prepare an assay sample by adding a reagent comprising a fluorescent dye to a blood specimen;
    a detection unit comprising a semiconductor laser light source configured to irradiate the assay sample with laser light; a first detector configured to detect scattered light emitted from particles within the assay sample irradiated by the laser light; and a second detector configured to detect fluorescent light emitted from particles within the assay sample irradiated by the laser light;
    a display; and
    a controller configured to:
        obtain a first signal indicative of scattered light intensities of the particles in the assay sample based on the detected scattered light;
        obtain a second signal indicative of fluorescent light intensities of the particles in the assay sample based on the detected fluorescent light;
        scale the first and second signals onto a two-dimensional scattergram that displays dots corresponding to the obtained scattered light intensities and the obtained fluorescent light intensities of the particles, wherein the scattergram comprises:
            a scattered light intensity and a fluorescent light intensity as coordinate axes;
            a predetermined immature platelets region; and
            a predetermined mature platelets region;
        determine a first count indicative of a number of the first and second signals scaled onto the predetermined immature platelets region of the two-dimensional scattergram;
        determine a second count indicative of a number of the first and second signals scaled onto the predetermined mature platelets region of the two-dimensional scattergram;
        determine whether a ratio of the first count over a sum of the first and second counts exceeds a predetermined threshold;
        output the prepared scattergram to the display; and
        output an indicator to the display if the ratio exceeds the predetermined threshold.

2. The apparatus of claim 1, wherein the fluorescent dye is capable of staining RNA within a cell, and is excitable so as to emit fluorescent light when irradiated by laser light from a semiconductor laser light source.

3. The apparatus of claim 2, wherein the fluorescent dye is represented by the structural formula:

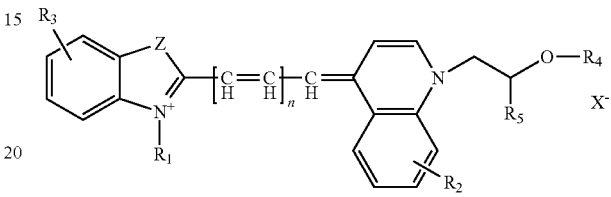

wherein R1 represents a hydrogen atom or lower alkyl group; R2 and R3 are independently selected from a hydrogen atom, a lower alkyl group, and a lower alkoxy group; R4 represents a hydrogen atom, acyl group, or lower alkyl group; R5 represents a hydrogen atom or substituted lower alkyl group; Z represents a sulfur atom, oxygen atom, or one or two lower alkyl group-substituted carbon atom; n represents 1 or 2; and X represents an anion.

4. The apparatus of claim 1, wherein the display comprises a liquid crystal touch panel.

5. The apparatus of claim 1, wherein the scattered light comprises forward scattered light.

6. The apparatus of claim 1, wherein the controller is further configured to:
    identify at least one disease associated with the blood specimen based on the ratio of the number of the first count over a sum of the first and second counts,
    wherein the indicator comprises an identification of the at least one disease.

7. The apparatus of claim 1, wherein the indicator comprises information identifying at least one disease associated with the blood specimen.

8. The apparatus of claim 1, wherein the first count is indicative of a number of immature platelets within the assay sample.

9. The apparatus of claim 1, wherein the second count is indicative of a number of mature platelets within the assay sample.

* * * * *